(12) United States Patent
Kano

(10) Patent No.: US 7,440,540 B2
(45) Date of Patent: Oct. 21, 2008

(54) STEREOSCOPIC X-RAY SYSTEM AND METHOD

(76) Inventor: Bassel Kano, 43 Concord Sq., Apt. 2, Boston, MA (US) 02118

( * ) Notice: Subject to any disclaimer, the term of this patent is extended or adjusted under 35 U.S.C. 154(b) by 51 days.

(21) Appl. No.: 11/539,007

(22) Filed: Oct. 5, 2006

(65) Prior Publication Data

US 2008/0095308 A1 Apr. 24, 2008

(51) Int. Cl.
*G21K 4/00* (2006.01)
*G21K 1/00* (2006.01)
*G21K 3/00* (2006.01)

(52) U.S. Cl. .......................... 378/41; 378/147; 378/156

(58) Field of Classification Search .................. 378/41, 378/62, 65, 98.12, 163, 205, 64, 147–156
See application file for complete search history.

(56) References Cited

U.S. PATENT DOCUMENTS

| | | | |
|---|---|---|---|
| 3,783,282 | A | 1/1974 | Hoppenstein |
| 5,448,610 | A | 9/1995 | Yamamoto et al. |
| 6,317,481 | B1 | 11/2001 | Berestov |
| 6,405,071 | B1 | 6/2002 | Analoui |
| 6,904,122 | B2 | 6/2005 | Swift et al. |
| 7,027,642 | B2 | 4/2006 | Rubbert et al. |
| 7,035,371 | B2 * | 4/2006 | Boese et al. ................... 378/41 |
| 7,227,925 | B1 * | 6/2007 | Mansfield et al. .............. 378/65 |
| 7,369,641 | B2 * | 5/2008 | Tsubaki et al. ................. 378/41 |
| 2003/0031291 | A1 | 2/2003 | Yamamoto et al. |
| 2003/0117702 | A1 | 6/2003 | Winterot et al. |
| 2005/0123180 | A1 | 6/2005 | Luo et al. |

FOREIGN PATENT DOCUMENTS

| | | |
|---|---|---|
| EP | 0088356 | 9/1983 |
| JP | 2000287958 | 10/2000 |

OTHER PUBLICATIONS

Hajeer, M. Y.; "Current Products and Practices, Applications of 3D imaging in orthodontics: Part I"; *Journal of Orthodontics*; vol. 31, 2004, pp. 62-70.
Koidis, P., et al.; "3D Visualization of Dental Data for Virtual Treatment Planning"; *The Aristotle University of Thessaloniki,*.
Dental Technology; "Intra-oral Camera, Virtual Reality I—glasses, CEREC 3, Digital X-rays"; Asavant Dental Clinic; http://ww.asavanant.com/DentalTechn.html, 2002.

* cited by examiner

*Primary Examiner*—Irakli Kiknadze
(74) *Attorney, Agent, or Firm*—Foley Hoag LLP

(57) ABSTRACT

Disclosed are systems and methods for obtaining stereoscopic x-ray images. The method includes taking two digital x-ray views of the same object from differing positions. The included angle between the axes of the x-rays for each position generally coincides with that formed by a pair of eyes viewing the object, though larger angles can be used. The x-rays can be taken by two x-ray generators within a single housing or within separate but attached housings. The generators are spaced apart and aimed at the object to form the appropriate angle. Care is taken not to move the object. Preferably, the x-ray generators have dual collimators to take the views. In this case, the time between taking the two x-rays need only be as long as the image capture time of the sensor being used, which lessens the chance of the object moving.

16 Claims, 2 Drawing Sheets

STEREOSCOPIC X-RAY SYSTEM AND METHOD

FIELD

The disclosed methods and systems relate to diagnostic imaging systems, and more specifically to systems and methods for obtaining stereoscopic x-ray images.

BACKGROUND

X-ray technology has found many practical uses in medical, industrial, and scientific fields. One of the more familiar uses of x-rays is as a diagnostic tool in the fields of medicine and dentistry. As such, x-rays are used to visualize anatomical structures and detect the presence of pathology, disease or abnormal anatomy. Advances in x-ray technology include the use of digital x-ray equipment, wherein images are captured digitally. The use of digital x-ray equipment can greatly reduce a patient's exposure to potentially harmful radiation, while providing sharper image detail and ease of processing.

However, the usefulness of x-ray technology has been limited by the difficulty in providing three-dimensional information of the object being examined. Studies in the field of dentistry have shown that for a more accurate diagnosis, two or three radiographs taken at different angles are necessary. Those radiographs are conventionally viewed individually by the examiner and processed and compared in the examiner's brain to be visualized in 3 dimensions.

Several systems have been devised to obtain three dimensional information, including transmission X-ray microscopes and Computerized Axial Tomography (CAT) scanners. These systems combine x-ray transmission systems with tomographical reconstruction methods to enable recreation of three-dimensional information from sets of flat cross-sectional images. The systems rely on a large number of different cross-sectional images of an object taken from many different angles. The digital image data is processed in a computer to yield a three-dimensional picture that can display the object being examined in great detail.

The systems, however, are complicated and generally expensive, making them somewhat inaccessible and unaffordable. In addition, the amount of the radiation necessary to produce a CAT image is very high compared to standard two-dimensional images. What is needed, then, is a system and method for extracting three-dimensional information from two-dimensional x-ray images that is relatively simple to use, is accessible and affordable, yet provides limited exposure of a patient or other object to radiation.

SUMMARY

Disclosed are systems and methods for obtaining stereoscopic x-ray images. The method includes taking two digital x-ray views of the same object from differing positions. The included angle between the axes of the x-rays for each position generally coincides with that formed by a pair of eyes viewing the object, though larger angles can be used. The x-rays can be taken by two x-ray generators within a single housing or within separate but attached housings. The x-ray generators are spaced apart and aimed at the object to form the appropriate angle. Care is taken not to move the object. Preferably, the x-ray generators have dual collimators to take the views. In this case, the time between taking the two x-rays need only be as long as the image capture time of the sensor being used, which lessens the chance of the object moving.

The digital data from the sensor for each position is processed in the normal manner to provide an image of the object from each position. The two resulting images are displayed in a manner such that only the image corresponding to the viewer's eye position is received at that eye. Current methods of displaying three-dimensional (3D) images can be used. For example, the images can be polarized and viewed through corresponding polarized eyeglasses. Preferably, the images can be displayed on a 3D liquid crystal display (LCD) screen, such as the Sharp Actius™ RD3D. On such screens, the two images are overlapped, but use separate pixels for each image. An LCD filter restricts the angle at which light from the pixels can be viewed, such that the image corresponding to the viewer's left eye can only be viewed by the left eye and vice versa. Other screens are formed with ridges that restrict the viewing angle for each pixel. Other means for viewing stereoscopic images include eyeglass video displays that present the separate images to the corresponding eye, or a 3D viewer using mirrors to reflect the corresponding image from two monitors to the respective eye of the viewer.

In one embodiment, a system for obtaining a stereoscopic x-ray image of a target includes at least one housing, a pair of spaced apart x-ray tubes within the at least one housing, each x-ray tube generating x-rays when energized, a collimator associated with each x-ray tube and a digital image sensor spaced opposite the target from the collimators. A longitudinal axis of each collimator is aligned between its associated x-ray tube and the target. Each collimator filters the x-rays from its associated x-ray tube such that x-rays not travelling towards the target are limited. The digital image sensor detects x-rays from the x-ray tubes and outputs sensor data for each x-ray tube for forming the stereoscopic x-ray image. In some aspects, the x-ray tubes may be located within a single housing.

In one aspect, the system can include a processor in communication with the digital image sensor to receive the sensor data and output image data, and a display in communication with the processor to receive the image data and output the stereoscopic x-ray image for viewing. The display can further include a filter to restrict viewing of a portion of the stereoscopic x-ray image corresponding to x-rays detected by the sensor from one of the x-ray tubes to viewing from one eye of a viewer wherein a position of the eye with respect to the display corresponding to a position of the one of the x-ray tubes with respect to the object. The display can be a liquid crystal display and the filter can restrict an angle at which light from a pixel of the liquid crystal display can be viewed. The display can be an eyeglass display having a separate display for each eye of a viewer, wherein each display presents a portion of the stereoscopic x-ray image corresponding to x-rays detected at the sensor from one of the x-ray tubes.

A transformer can convert incoming power to a voltage differential required to energize the x-ray tubes to emit x-rays. A power switch can be configured to limit the incoming power. A transfer switch can be configured to transfer energizing power from one x-ray tube to the other x-ray tube. A timer can be configured to activate the transfer switch.

In one embodiment, a method of obtaining a stereoscopic x-ray image of a target can include energizing a first x-ray tube to emit x-rays in a direction towards the target, energizing a second x-ray tube spaced apart from the first x-ray tube to emit x-rays in a direction towards the target, detecting emitted x-rays at a sensor to obtain sensor data, processing the sensor data to obtain image data and displaying the image data to provide a stereoscopic x-ray image of the target. In some aspects, the method can include maintaining the positions of the first and second x-ray tubes, the sensor and the target during energizing and detecting.

The method can include connecting to a power supply and transforming power from the power supply to provide a differential voltage at the x-ray tubes sufficient to energize the x-ray tubes. The method can include limiting the power from the power supply to that required for energizing the first and the second x-ray tubes.

In one aspect, detecting can include downloading the sensor data obtained by detecting the x-rays emitted from the first x-ray tube to a processor and downloading the sensor data obtained by detecting the x-rays emitted from the second x-ray tube to the processor. Prior to energizing the second x-ray tube, power to the first x-ray tube may be cut and the sensor data obtained by detecting the x-rays emitted from the first x-ray tube can be cleared from the sensor.

In one aspect, displaying can include filtering the stereoscopic x-ray image to restrict viewing of a portion of the stereoscopic x-ray image corresponding to x-rays detected by the sensor from one of the x-ray tubes to viewing from one eye of a viewer at a position of the eye with respect to the display corresponding to a position of the one of the x-ray tubes with respect to the object. Filtering can include restricting an angle at which light from a pixel of a liquid crystal display can be viewed.

In one aspect, displaying can include displaying a first portion of the stereoscopic x-ray image corresponding to x-rays detected by the sensor from the first x-ray tube to a first eye of a viewer and displaying a second portion of the stereoscopic x-ray image corresponding to x-rays detected by the sensor from the second x-ray tube to a second eye of the viewer.

DESCRIPTION

To provide an overall understanding, certain illustrative embodiments will now be described; however, it will be understood by one of ordinary skill in the art that the apparatus described herein can be adapted and modified to provide apparatus for other suitable applications and that other additions and modifications can be made without departing from the scope of the systems and methods described herein.

Unless otherwise specified, the illustrated embodiments can be understood as providing exemplary features of varying detail, and therefore, unless otherwise specified, features, components, modules, and/or aspects of the illustrations can be otherwise combined, separated, interchanged, and/or rearranged without departing from the disclosed systems or methods. Additionally, the shapes and sizes of components are also exemplary and unless otherwise specified, can be altered without affecting the disclosed systems or methods. Throughout the entirety of the present disclosure, use of the articles "a" or "an" to modify a noun can be understood to be used for convenience and to include one, or more than one of the modified noun, unless otherwise specifically stated.

Figure 1:
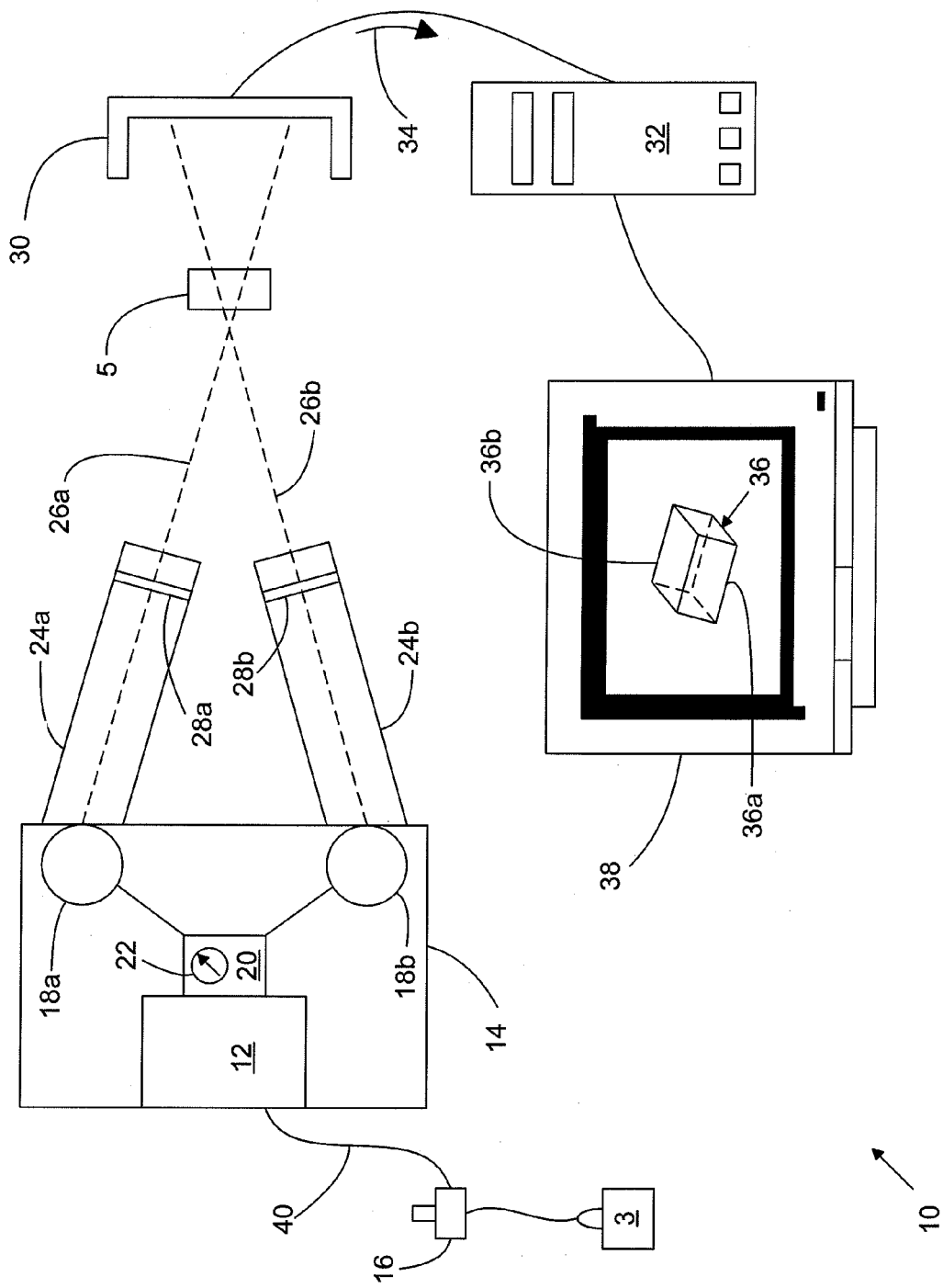
FIG. 1 is a schematic representation of a stereoscopic x-ray system.

FIG. 1 illustrates a schematic representation of a system 10 for producing stereoscopic x-ray images. A transformer 12 within housing 14 of system 10 is connected to a power supply 3 via power switch 16. Power switch 16 may be remotely located so as not to expose an operator to radiation. Transformer 12 converts incoming power from power supply 3 to provide a high voltage differential across the electrode pairs (not shown) of x-ray tubes 18a and 18b. X-ray tubes 18a, 18b operate in the manner of known x-ray tubes to emit x-rays. For example, current to the cathode of the electrode pair heats a filament, which sputters electrons to a tungsten anode at high speed. A high speed electron can knock loose an electron from a tungsten atom's lower orbital and an electron from a higher orbital can fall to the lower energy level, releasing a high energy x-ray photon. Transfer switch 20 can transfer current from x-ray tube 18a to x-ray tube 18b and vice versa. Switch 20 can include timer 22 for automatic transfer of current.

Collimator tubes 24a, 24b absorb unwanted x-rays to effectively limit the emitted x-rays to a direction along their longitudinal axes 26a, 26b. In this manner, the emitted x-rays are filtered so that only those travelling essentially parallel to axes 26a, 26b and generally convergent on target 5 are allowed through the collimator tubes 24a, 24b. Pure aluminum disks 28a, 28b may be placed in the path of the x-ray beams to filter out low energy x-rays whose wave lengths are such that they would not penetrate the object and hence would not be useful for producing images. Image sensor 30 digitally captures the x-ray photons passing through object 5 and the digital sensor data captured by sensor 30 is input to processor 32 (as illustrated by arrow 34). Processor 32 processes the sensor data obtained from each x-ray tube 18a, 18b to obtain image data for a pair of two-dimensional images 36a, 36b that are displayed on display 38.

The two resulting images 36a, 36b are displayed in a manner such that only the image for the x-ray tube corresponding to the viewer's eye position is received at that eye, thus providing a 3D image 36 to the user. Known methods for displaying 3D images may be utilized. For example, the images can be polarized and/or colored and viewed through corresponding polarized and/or colored eyeglasses. Preferably, the images can be displayed on a 3D LCD screen, such as the Sharp Actius™ RD3D. On such screens, the two images are overlapped, but use separate pixels for each image. An LCD filter restricts the angle at which light from the pixels can be viewed, such that the image corresponding to the viewer's left eye can only be viewed by the left eye and vice versa. Other types of displays include screens formed with ridges that restrict the viewing angle for each pixel; eyeglass video displays that present the separate images to the corresponding eye; 3D viewers using mirrors to reflect the corresponding image from two monitors to the respective eye of the viewer; and other means as are known in the art.

Figure 2:
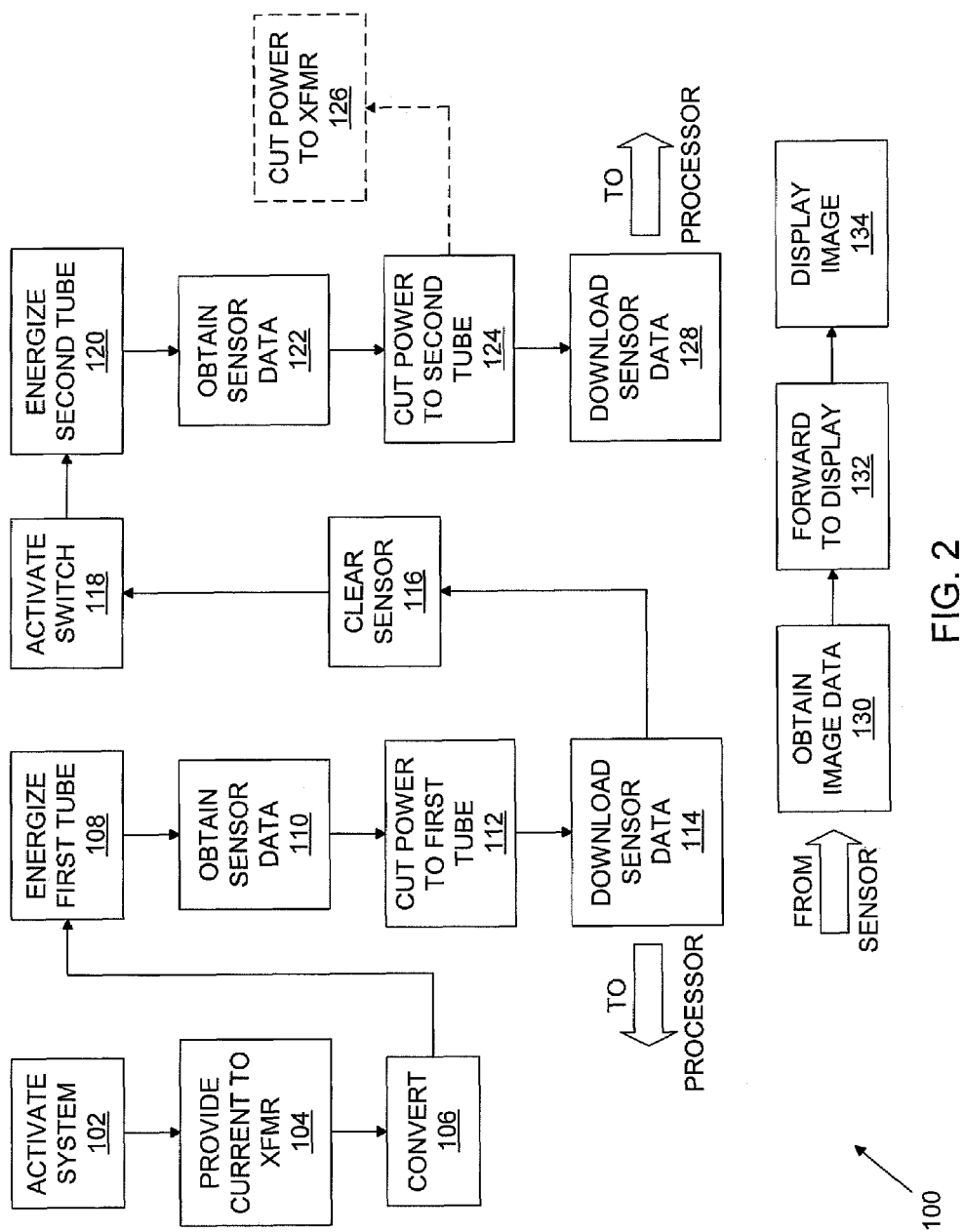
FIG. 2 is a block diagram of a method for providing stereoscopic x-ray images.

FIG. 2 is a block diagram of a method 100 by which system 10 provides stereoscopic x-ray images for viewing. X-ray system 10 is activated (102) using power switch 16. When system 10 is activated, current flows (104) to transformer 12. Power switch 16 may limit the amount of current that flows to transformer 12 to that required for system 10 to obtain the image data for forming the stereoscopic image. Power switch 16 may work in conjunction with transfer switch 20 and timer 22 to limit the total time of exposure, i.e., the time during which the object 5 is exposed to x-rays. Transformer 12 converts (106) the incoming power to provide the necessary high voltage differential across the electrode pairs of a first of the x-ray tubes 18a, 18b so as to energize (108) the tube. For the sake of illustration, but not limitation, the systems and methods are described herein with x-ray tube 18a being the first energized x-ray tube and x-ray tube 18b being the second energized x-ray tube. It will be understood that the order in which the x-ray tubes are energized does not affect the operation of the systems or methods described.

When x-ray tube 18a has been energized for a time sufficient to obtain sensor data at image sensor 28 for forming a digital image, as determined by timer 22 at block 110, switch 20 is activated to cut power to x-ray tube 18a, as at block 112. Image sensor 28 may download (114) the sensor data obtained from x-rays emanating from x-ray tube 18a to processor 30. After a time sufficient for image sensor 28 to clear, as determined by timer 22 at block 116, switch 20 is activated (118) such that the output from transformer 12 is directed to x-ray tube 18b to energize x-ray tube 18b (120).

When x-ray tube 18b has been energized for a time sufficient to obtain sensor data at image sensor 28 for forming a digital image, as determined by timer 22 at block 122, switch 20 is activated to cut power to x-ray tube 18b, as at block 124. Timer 22 may operate in conjunction with switch 16 to limit power to transformer 12, such that when power to x-ray tube 18b is cut, switch 16 may be activated to cut power to transformer 12, as indicated by dashed block 126. Switch 16 may independently cut power to transformer 12 after a preset amount of time as a fail-safe measure.

Image sensor 28 may download (128) the sensor data obtained from x-rays emanating from x-ray tube 18b to processor 30. For illustration purposes, downloading of the sensor data from image sensor 28 to processor 30 (blocks 114, 128) is shown following the cutting of power to x-ray tubes 18a, 18b. However, depending on the configuration of image sensor 28 and processor 30, image sensor 28 may download the sensor data to processor 30 while x-ray tubes 18a, 18b are energized or both during and after x-ray tubes 18a, 18b are energized.

Processor 30 processes (130) the sensor data to obtain image data corresponding to a two-dimensional x-ray image for x-ray tube 18a and a two-dimensional x-ray image for x-ray tube 18b. The image data is forwarded (132) to display 36. Using the image data from processor 30, display 36 displays (134) the image data such that a viewer perceives a 3D x-ray image of the target, as described with relation to display 36.

Although the stereoscopic x-ray system and method have been described relative to specific embodiments thereof, they are not so limited. Obviously many modifications and variations may become apparent in light of the above teachings. For example, timer 22 can be configured with power switch 16, or separately along power line 40 feeding transformer 12. Alternately, x-ray tubes 24a, 24b may each be located within a housing that may be attached together to form housing 14. Similarly, each x-ray tube 24a, 24b may have its own transformer 12 and transfer switch 20 may be configured with power switch 16 to transfer power between the transformers 12. Elements, components, modules, and/or parts thereof that are described and/or otherwise portrayed through the figures to communicate with, be associated with, and/or be based on, something else, can be understood to so communicate, be associated with, and or be based on in a direct and/or indirect manner, unless otherwise stipulated herein.

Many additional changes in the details, materials, and arrangement of parts, herein described and illustrated, can be made by those skilled in the art.

What is claimed is:

1. A system for obtaining a stereoscopic x-ray image of a target, comprising:
   at least one housing;
   a pair of spaced apart x-ray tubes within the at least one housing, each x-ray tube generating x-rays when energized;
   a collimator associated with each x-ray tube, a longitudinal axis of each collimator being aligned between its associated x-ray tube and the target, each collimator filtering the x-rays from its associated x-ray tube such that x-rays not travelling towards the target are limited; and
   a digital image sensor spaced opposite the target from the collimators, the digital image sensor for detecting x-rays from the x-ray tubes and outputting sensor data for each x-ray tube for forming the stereoscopic x-ray image.

2. The system of claim 1, further comprising:
   a processor in communication with the digital image sensor, the processor receiving the sensor data and outputting image data; and
   a display in communication with the processor, the display receiving the image data and outputting the stereoscopic x-ray image for viewing.

3. The system of claim 2, wherein the display further comprises a filter to restrict viewing of a portion of the stereoscopic x-ray image corresponding to x-rays detected by the sensor from one of the x-ray tubes to viewing from one eye of a viewer, a position of the eye with respect to the display corresponding to a position of the one of the x-ray tubes with respect to the object.

4. The system of claim 3, wherein the pair of spaced apart x-ray tubes are located within a single housing.

5. The system of claim 3, wherein the display further comprises:
   a liquid crystal display; and
   the filter restricts an angle at which light from a pixel of the liquid crystal display can be viewed.

6. The system of claim 5, further comprising a transformer to convert incoming power to a voltage differential required to energize the x-ray tubes to emit x-rays.

7. The system of claim 6, further comprising a power switch configured to limit the incoming power.

8. The system of claim 5, further comprising a transfer switch configured to transfer energizing power from one x-ray tube to the other x-ray tube; and a timer configured to activate the transfer switch.

9. The system of claim 5, wherein the pair of spaced apart x-ray tubes are located within a single housing.

10. The system of claim 2, wherein the display comprises an eyeglass display having a separate display for each eye of a viewer, each display presenting a portion of the stereoscopic x-ray image corresponding to x-rays detected by the sensor from one of the x-ray tubes.

11. The system of claim 2, wherein the display comprises:
    a first display for displaying a portion of the stereoscopic x-ray image corresponding to x-rays detected by the sensor from a first of the x-ray tubes;
    a second display for displaying a portion of the stereoscopic x-ray image corresponding to x-rays detected by the sensor from a second of the x-ray tubes; and
    means to separately direct images from the first and the second displays to respective eyes of a viewer.

12. The system of claim 1, further comprising a transformer to convert incoming power to a voltage differential required to energize the x-ray tubes to emit x-rays.

13. The system of claim 12, further comprising a power switch configured to limit the incoming power.

14. The system of claim 1, further comprising a transfer switch configured to transfer energizing power from one x-ray tube to the other x-ray tube.

15. The system of claim 14, further comprising a timer configured to activate the transfer switch.

16. The system of claim 1, wherein the pair of spaced apart x-ray tubes are located within a single housing.

* * * * *